US009833339B2

(12) United States Patent
Froidevaux et al.

(10) Patent No.: US 9,833,339 B2
(45) Date of Patent: Dec. 5, 2017

(54) INSERT PRESS AND RELATED METHOD

(71) Applicant: Zimmer, Inc., Warsaw, IN (US)

(72) Inventors: Rolf Froidevaux, Warsaw, IN (US); Paul Borries, Columbia City, IN (US)

(73) Assignee: ZIMMER, INC., Warsaw, IN (US)

( * ) Notice: Subject to any disclaimer, the term of this patent is extended or adjusted under 35 U.S.C. 154(b) by 306 days.

(21) Appl. No.: 14/609,662

(22) Filed: Jan. 30, 2015

(65) Prior Publication Data

US 2015/0230939 A1    Aug. 20, 2015

Related U.S. Application Data

(60) Provisional application No. 61/941,839, filed on Feb. 19, 2014.

(51) Int. Cl.
| | | |
|---|---|---|
| *B30B 1/18* | (2006.01) | |
| *B30B 1/20* | (2006.01) | |
| *A61F 2/46* | (2006.01) | |
| *B25B 27/02* | (2006.01) | |
| *B25B 5/16* | (2006.01) | |
| *B25B 5/10* | (2006.01) | |
| *A61F 2/30* | (2006.01) | |
| *A61F 2/32* | (2006.01) | |

(52) U.S. Cl.
CPC ............ *A61F 2/4637* (2013.01); *B25B 5/101* (2013.01); *B25B 5/163* (2013.01); *B25B 27/023* (2013.01); *B30B 1/18* (2013.01); *B30B 1/20* (2013.01); *A61F 2002/30507* (2013.01); *A61F 2002/3208* (2013.01); *Y10T 29/4987* (2015.01); *Y10T 29/49876* (2015.01); *Y10T 29/53848* (2015.01)

(58) Field of Classification Search
CPC .......... B30B 1/18; B30B 1/20; B30B 9/3064; B25B 27/023; B25B 5/101; B25B 5/163; A61F 2/4637; A61F 2002/3208; A61F 2002/305; A61F 2002/307; Y10T 29/4987; Y10T 29/49876; Y10T 29/53848; F16B 37/08; F16B 37/0807; F16B 37/0821; F16B 37/0828; F16B 37/0842; F16B 37/0878; F16B 37/0885; F16B 37/0892; F16B 37/0857; F16B 37/0864; F16B 37/0871
USPC ........................................... 100/289; 29/256
See application file for complete search history.

(56) References Cited

U.S. PATENT DOCUMENTS

| | | | | |
|---|---|---|---|---|
| 602,088 | A | * | 4/1898 | Morgan ................ A47J 19/022 100/132 |
| 1,543,036 | A | * | 6/1925 | Taylor ..................... A47J 27/20 100/125 |
| 2,789,458 | A | * | 4/1957 | Skeisvoll ............ F16B 37/0821 411/433 |

(Continued)

OTHER PUBLICATIONS

"Stafit Acetabular System: Surgical Technique", Zimmer, Inc., (2009), 20 pgs.

*Primary Examiner* — Jimmy T Nguyen
(74) *Attorney, Agent, or Firm* — Schwegman Lundberg & Woessner, P.A.

(57) ABSTRACT

An insert press that has a threaded shaft with a distal end is disclosed. An insert driver is disposed at the distal end of the threaded shaft. The insert press also includes a press housing that provides a bore through which the threaded shaft extends. The bore is transformable from a first condition in which the threaded shaft is threadably translatable in the bore to a second condition in which the threaded shaft is non-threadably translatable in the bore.

17 Claims, 11 Drawing Sheets

(56) References Cited

U.S. PATENT DOCUMENTS 3,820,454 A * 6/1974 Uchida .................... B30B 1/18
                                                 100/116
4,290,499 A    9/1981 Luomaranta
7,416,143 B1 * 8/2008 Leyshon ............... A61J 7/0007
                                                 100/233

* cited by examiner

INSERT PRESS AND RELATED METHOD

CLAIM OF PRIORITY

This application claims the benefit of U.S. Provisional Patent Application Ser. No. 61/941,839, filed on Feb. 19, 2014, the benefit of priority of which is claimed hereby, and which is incorporated by reference herein in its entirety.

TECHNICAL FIELD

This patent document pertains generally, but not by way of limitation, to presses for installing inserts or trial inserts on a prosthetic implant.

BACKGROUND

In many surgical procedures, time can literally be a matter of life and death. Any device or instrument that can perform a function more efficiently, produce any time savings, or require lesser numbers of personnel can be greatly beneficial. In a hip replacement surgery for example, an articulating member, such as a polymer insert may need to be pressed onto a metallic femoral head member. The femoral head member can be spherical and if the insert is not placed and held in the correct position before being engaged by a press, it can slip to one side and installation of the insert can be problematic. In the case of a prior art press, Zimmer Cup Assembly Press, part number 0.100489.900 having a ratcheting type press shaft, a surgeon can require an assistant to hold an insert in place over the femoral head during the insert pressing procedure.

OVERVIEW

The present inventors recognize, among other things, that an insert press that can be operated by one person, maintain the proper orientation of an insert on a prosthetic component, provide quick release and fast initial set up would be beneficial. Aspects of The present disclosure can be a solution to these requirements through providing an insert press such as a screw type insert press. A disclosed insert press can include a press housing having a transformable bore.

In the present disclosure a distal direction is defined as a direction towards a base of the insert press along an axis of a threaded shaft and a proximal direction is defined as a direction away from the insert press base along the axis of the threaded shaft.

The present disclosure provides, in certain aspects, an insert press having a press housing including a bore through which a threaded shaft extends. The press housing can be configured to allow the bore to change or transform from one shape, condition or configuration to another shape, condition or configuration. For example, a first condition can allow the threaded shaft to move or translate threadably. The threads of the threaded shaft can be mated with threads in the press housing and the threaded shaft can be rotated. The rotation will either move the threaded shaft up or down or in the case of the insert press either distally or proximally. In such a first condition, because of the mated threads, the shaft cannot move distally or proximally without rotation of the threaded shaft relative to the insert press housing. If the press housing has been transformed to a second condition, the threads in the press housing no longer engage the threads of the threaded shaft in the same manner, or at all. For example, the bore might now be large enough to allow the threaded shaft to be translated non-threadably, in other words, the threaded shaft can be moved in a proximal or distal direction without rotation of the threaded shaft. The bore can be transformed from a first condition to a second condition in a variety of ways or methods and any examples presented here are not meant to be construed as limiting.

Femoral head prosthetics can be configured in at least two main types: a monoblock assembly that may require an in situ pressing of an insert onto a femoral head; and a multi-piece prosthetic whereby the femoral head is removable from the stem of the prosthetic and can have the insert pressed on in a location that is remote from the patient. In cases of revision hip arthroplasty, the surgeon may elect to leave the removable femoral head on the stem or may be unable to remove the head from the stem, in which case the multi-piece prosthetic may require in situ pressing of an insert onto the femoral head. In the remote application for example, a surgeon can use an insert press on a surgical table near the patient. The surgeon or a technician can place an insert over a spherical femoral head situated on a post in a lower member of a press. As a trigger mechanism is retracted, a threaded shaft can be allowed to drop into position and an insert driver member can engage a polymer insert and keep the insert in its proper position. At this point, the surgeon can remove a hand holding the insert in place and operate the press to push the insert over the femoral head. Although many of the examples disclosed in this document relate to femoral prosthetics, the insert press disclosed in this document can be used in prosthetic devices or methods relating to any joint of a human or animal body such as shoulder prosthesis.

To further illustrate the insert press and related kit, and method disclosed herein, a non-limiting list of examples is provided here:

In Example 1, an insert press can comprise: a threaded shaft having a distal end; an insert driver disposed at the distal end of the threaded shaft; and a press housing. The press housing can provide a bore through which the threaded shaft extends, the bore transformable from a first condition in which the threaded shaft is threadably translatable in the bore to a second condition in which the threaded shaft is non-threadably translatable in the bore.

In Example 2, the insert press of Example 1 can optionally be configured such that the bore is transformable from the first condition to the second condition by movement of at least one wall section of the bore having a surface with non-circumferential threads.

In Example 3, the insert press of Example 1 can optionally be configured such that the bore is transformable from the first condition to the second condition by movement of at least two wall sections of the bore that each have a surface with non-circumferential threads.

In Example 4, the insert press of any one or any combination of Examples 1-3 can optionally be configured such that the press housing further comprises a lower member having a forward end and a rear end; a handle member having a distal end and a proximal end, wherein the distal end extends from the rear end of the lower member; a body member having a threaded shaft end and a handle end, wherein the handle end extends from the proximal end of the handle member; and a trigger member engaging the body member and movable relative to the body member.

In Example 5, the insert press of any one or any combination of Examples 1-4 can optionally be configured such that the press housing further comprises a body member and a trigger member, wherein the bore is partially provided by the body member and partially provided by the trigger member.

In Example 6, the insert press of any one or any combination of Examples 4-5 can optionally be configured such that the body member provides a bore surface having non-circumferential threads.

In Example 7, the insert press of any one or any combination of Examples 4-5 can optionally be configured such that the trigger member provides a bore surface having non-circumferential threads.

In Example 8, the insert press of any one or any combination of Examples 4-5 can optionally be configured such that the body member provides a bore surface having non-circumferential threads and the trigger member provides a bore surface having non-circumferential threads and wherein when the bore is transformed into the first condition the non-circumferential threads of the body member engage a side of the threaded shaft and the non-circumferential threads of the trigger member engage an opposing side of the threaded shaft.

In Example 9, the insert press of any one or any combination of Examples 4-8 can optionally be configured such that the trigger member further comprises an aperture through which the threaded shaft extends, wherein the aperture and the bore are coaxial, the aperture sized to allow the threaded shaft to non-threadably translate in the bore when the bore is in the second condition.

In Example 10, the insert press of any one or any combination of Examples 4-9 can optionally be configured such that the trigger member further comprises a shaft end and a lever end, wherein the shaft end provides a shelf member having a horizontal surface and a vertical surface, the vertical surface comprising the non-circumferential threads of the bore surface provided by the trigger member which engage the threaded shaft in the first condition.

In Example 11, the insert press of any one or any combination of Examples 4-10 can optionally be configured to further comprise a latching means engaging the press housing body and configured to engage the trigger member and secure the trigger member in the first condition.

In Example 12, the insert press of Example 11 can optionally be configured such that the latching means engages the trigger member at a latch boss which extends from a surface of the trigger member.

In Example 13, the insert press of any one or any combination of Examples 4-12 can optionally be configured to further comprise a biasing means that biases the trigger member in the first condition.

In Example 14, the insert press of any one or any combination of Examples 1-13 can optionally be configured to further comprise a table base configured to engage with and stabilize the press housing.

In Example 15, a method of installing an insert can comprise: providing a press housing having a bore through which a threaded shaft extends, the bore transformable from a first condition in which the threaded shaft is threadably translatable in the bore to a second condition in which the threaded shaft is non-threadably translatable in the bore; providing an insert over a prosthetic component; transforming the bore to the first condition; threadably translating the threaded shaft in a direction towards the insert; engaging the insert with an insert driver located at a distal end of the threaded shaft; and pressing the insert on to the prosthetic component.

In Example 16, the method of installing an insert of Example 15 can optionally be configured such that the press housing further comprises a body member and a trigger member and wherein the bore is partially provided by the body member and partially provided by the trigger member.

In Example 17, the method of installing an insert of Example 16 can optionally be configured such that the body member provides a bore surface including non-circumferential threads.

In Example 18, the method of installing an insert of Example 16 can optionally be configured such that the trigger member provides a bore surface including non-circumferential threads.

In Example 19, the method of installing an insert of Example 16 can optionally be configured such that the body member provides a bore surface including non-circumferential threads and the trigger member provides a bore surface including non-circumferential threads.

In Example 20, the method of installing an insert of any one or any combination of Examples 15-19 can optionally be configured such that the prosthetic component is a femoral head.

In Example 21, the insert press and method of any one or any combination of Examples 1-20 can optionally be configured such that all elements, operations, or other options recited are available to use or select from.

These and other examples and features of the insert press and related method will be set forth in part in the following Detailed Description. This Overview is intended to provide non-limiting examples of the present subject matter—it is not intended to provide an exclusive or exhaustive explanation. The Detailed Description below is included to provide further information about the present insert press and related method.

BRIEF DESCRIPTION OF THE DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

DETAILED DESCRIPTION

In some surgical procedures, it can be important to be able to change or install modular devices quickly, such as in the case of a proximal femoral prosthesis having a separate insert member pressed onto a metallic or ceramic femoral head member. The insert press described in this application can be operated in situ on a patient after a prosthetic component is installed in a bone or the insert press can be operated on prosthetic component, such as a femoral head, on a table or other location remote from a patient.

The present disclosure includes an insert press which has a transformable bore mechanism that can allow a threaded shaft to be quickly positioned to install an insert on a prosthetic component and quickly released to allow a surgeon or technician to remove the press from the insert installation procedure.

In the following Detailed Description, it is to be understood that the insert press can be configured to operate with any suitable device for which such a quick connection/release would be beneficial, including prosthetic components.

The insert press and its components can be made of a wide variety of materials, such as metal alloys, stainless steels, aluminum, titanium, polymers, plastics, ceramics, or carbon fiber.

Figure 1A:
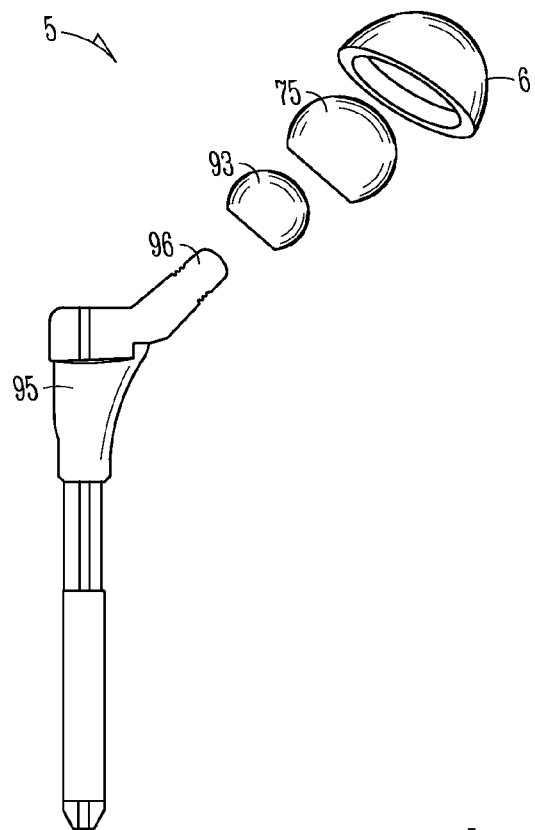
FIG. 1A illustrates an exploded view of a hip prosthesis.
Figure 1B:
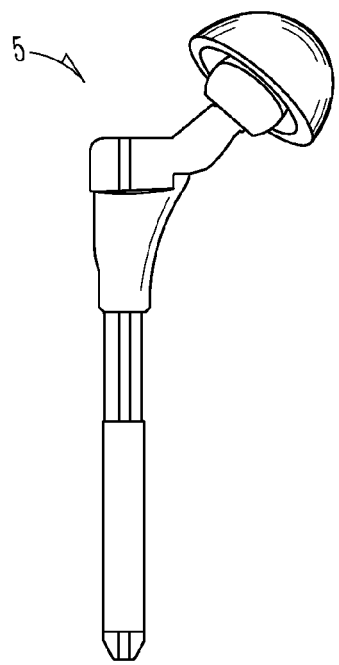
FIG. 1B illustrates an assembled view of a hip prosthesis.

FIG. 1A illustrates an exploded view of a hip prosthesis assembly 5. The hip prosthesis assembly 5 can include an acetabular cup 6 which forms an articular member of a hip replacement. An insert 75 can be partially spherically shaped and can be made of polyurethane or other plastic, polymer, composite, synthetic material, ceramic, or metal. The insert 75 can be manufactured to tightly fit over a prosthetic component such as a femoral head 93 which can be metallic, ceramic, polymer, plastic or other synthetic material. The insert 75 can form an articulating member of a hip prosthesis assembly 5. The femoral head 93 can be integral with the femoral stem 95 or as illustrated can be modular and fit, for example, tightly to a femoral head post 96. FIG. 1B illustrates an assembled view of the hip prosthesis assembly 5 as it might appear installed in a patient. The illustration of the femoral joint components is an example and the present disclosure can be applied to any femoral prosthesis or any other prosthetic component and is not limited to hip replacement components.

Figure 2:
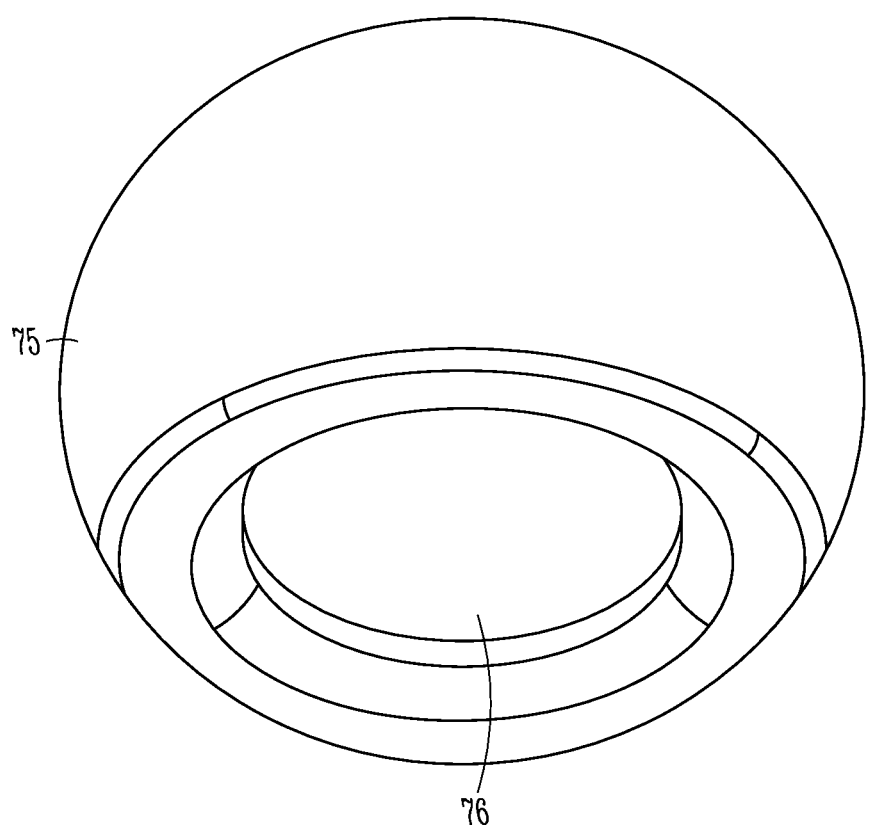
FIG. 2 illustrates an isometric view of a femoral insert as constructed in accordance with at least one embodiment.

FIG. 2 is a close up illustration of an insert 75. The insert 75 can include a head cavity 76 that can be sized and shaped to receive a portion of a prosthetic component, such as a femoral head 93 (See FIG. 1A).

Figure 3:
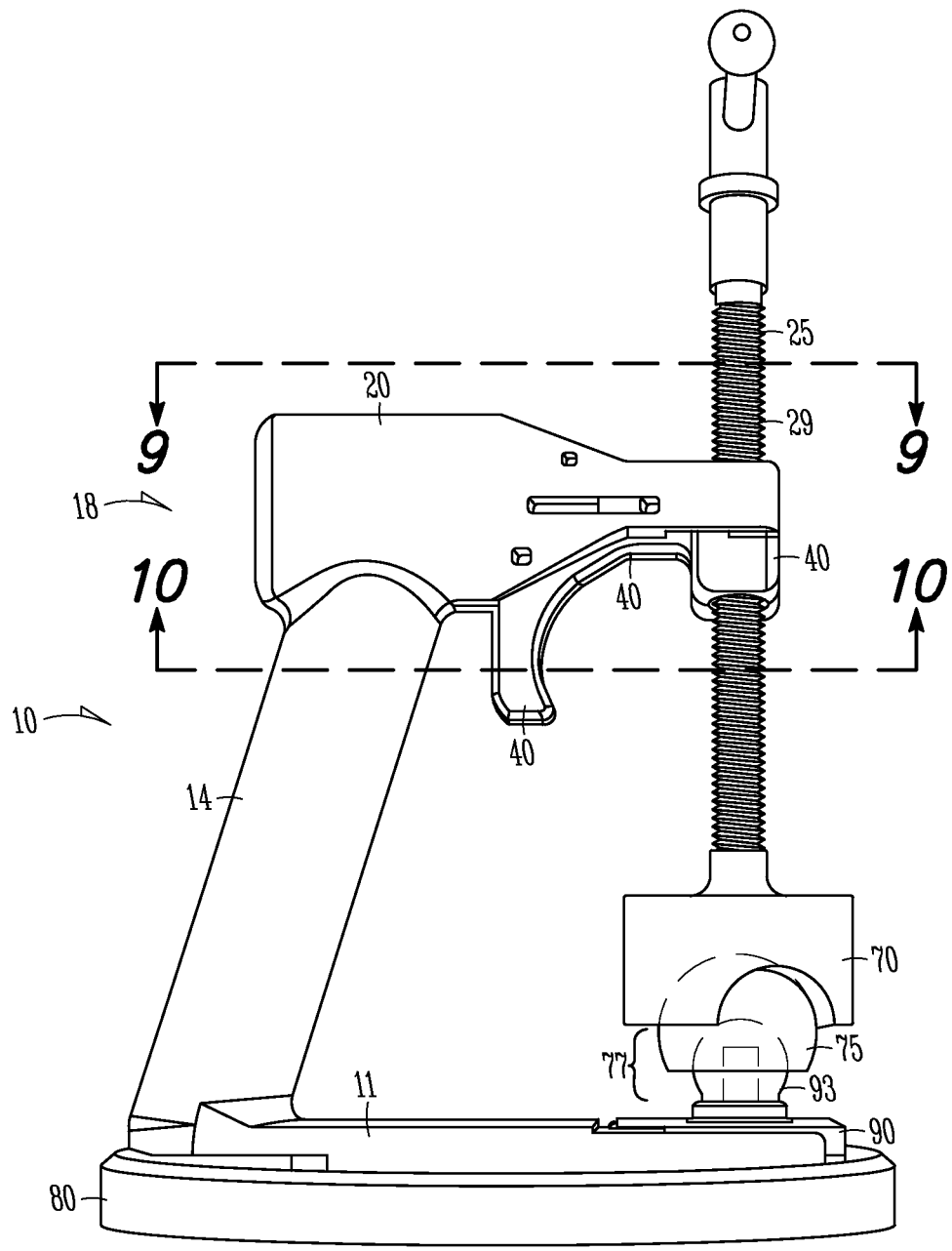
FIG. 3 illustrates an isometric view of an insert press used remotely from a patient, as constructed in accordance with at least one embodiment.

FIG. 3 is an illustration of the operation of an insert press 10. The insert press 10 can be installed in a table base 80 and be operated on a flat surface. The insert press 10 can include structures such as a press housing 18. The press housing 18 can include members such as a body member 20, a handle member 14, a lower member 11, and a trigger member 40 which will be described in more detail later in this document. An insert 75 can be placed over a prosthetic component such as a femoral head 93 which can be removably installed on an insert press post 98. The insert press 10 can include a threaded shaft 25 that can be rotated to cause downward movement of an insert driver 70. The insert driver 70 can engage the insert 75 and forcibly press it onto the femoral head 93. Once the insert 75 has been installed, a bore through which the threaded shaft 25 extends can be transformed from a first condition 7 in which threads from the press housing 18 are engaged or mated with shaft threads 29 from the threaded shaft 25 (See FIG. 7B) to a second condition 8 (See FIG. 7A). In the second condition 8 the shaft threads 29 of the threaded shaft 25 are not engaged with threads in the press housing 18 and the threaded shaft 25 can be quickly raised to allow the removal of the prosthetic component/insert assembly 77 from the insert press post 98. The inset press post 98 can be part of a cone adapter 90 (described more fully below).

Figure 4:
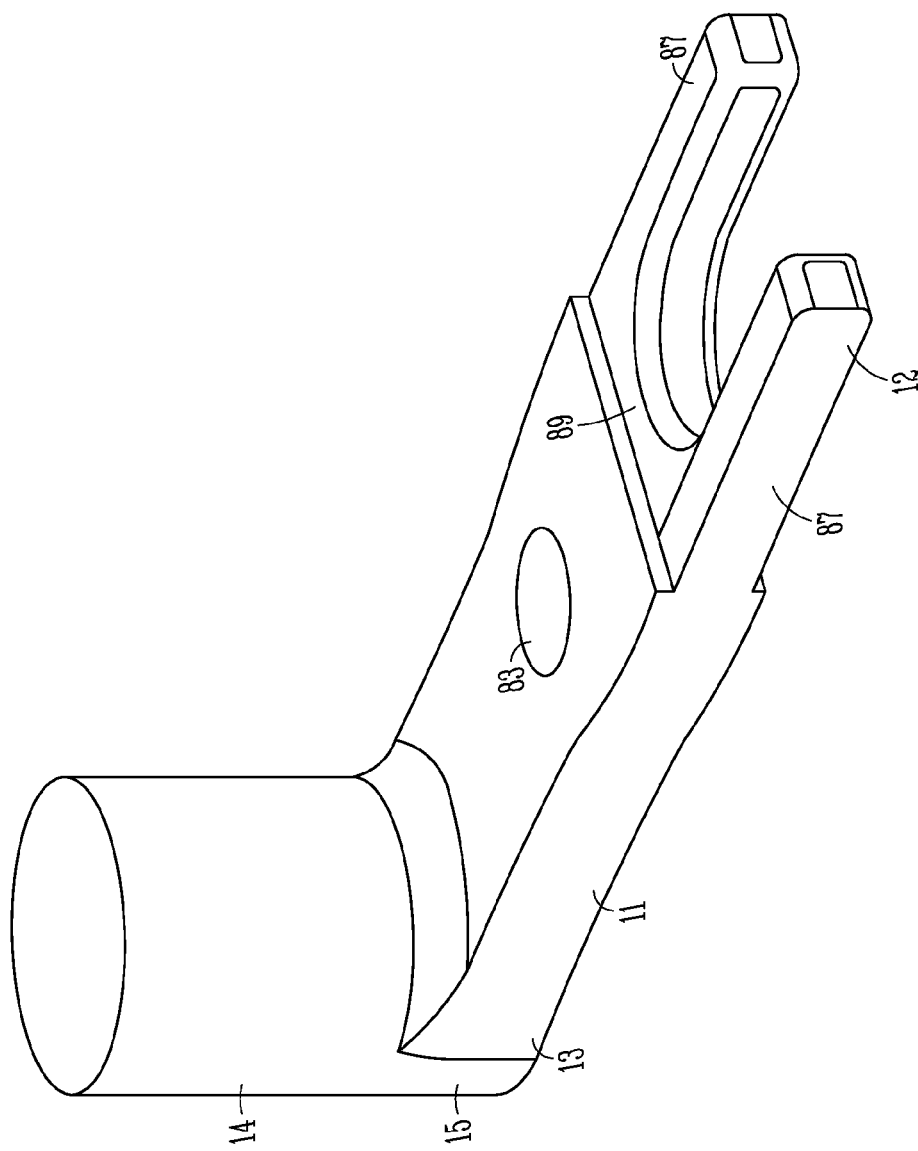
FIG. 4 illustrates a close up isometric view of an insert press lower member, as constructed in accordance with at least one embodiment.

FIG. 4 illustrates a close up view of an example of the lower member 11 of an insert press 10. At the forward end 12 of the lower member 11, the insert press 10 (See FIG. 3) can include a forked member 89 that can be configured to receive a cone adapter 90 (See FIG. 3) or a padded forked attachment 91 (See FIG. 5.). Either of these attachments can be slidably installed on the forks 87 of the forked member 89. The lower member 11 can include structure having a lower member aperture 83 which can aid in securing the insert press 10 to the table base 80 (See FIG. 3). The lower member 11 can have similar mating structures to stabilize the insert press 10 to the table base 80 such as a protrusion of any shape and a mating cavity that could be interchanged between the table base 80 and the lower member 11.

Figure 5:
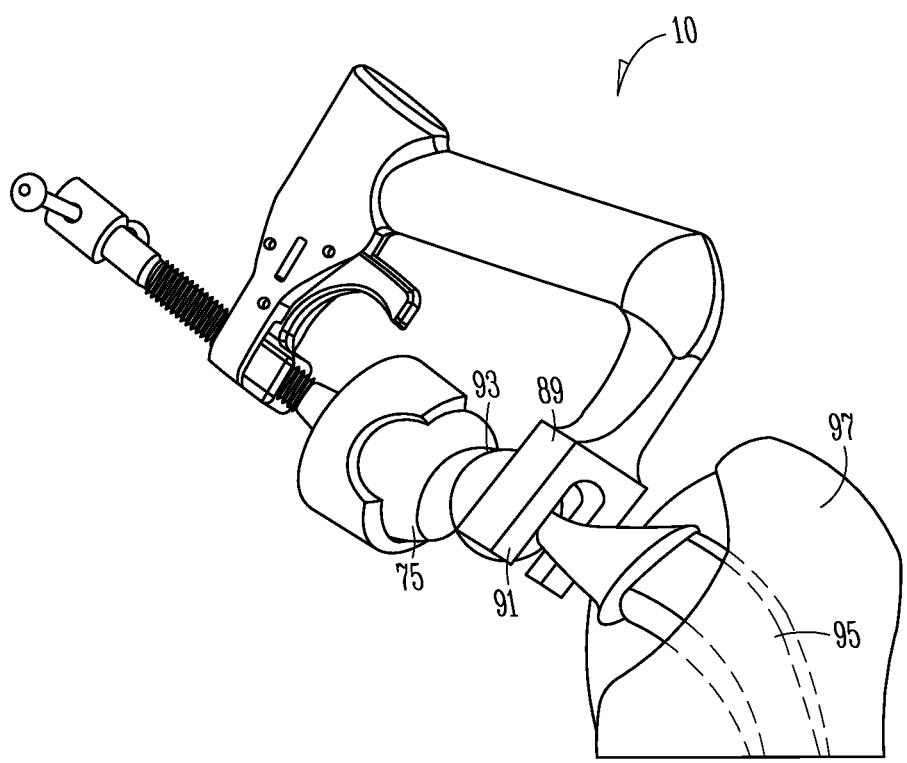
FIG. 5 illustrates an isometric view of an insert press used in situ on a patient, as constructed in accordance with at least one embodiment.

FIG. 5 illustrates an example operation of the insert press 10 in situ after a prosthetic component such as a femoral stem 95 has been installed in a femur 97. The insert press 10 can be removed from the table base 80 (See FIG. 3) and instead of a cone adapter 90 attached to the forked member 89, a padded forked attachment 91 can be placed on the forked member 89. The padded forked attachment 91 can engage lower surfaces of the femoral head 93 and provide stability to the insert press 10 as the insert 75 is pressed into place on the femoral head 93

Figure 6:
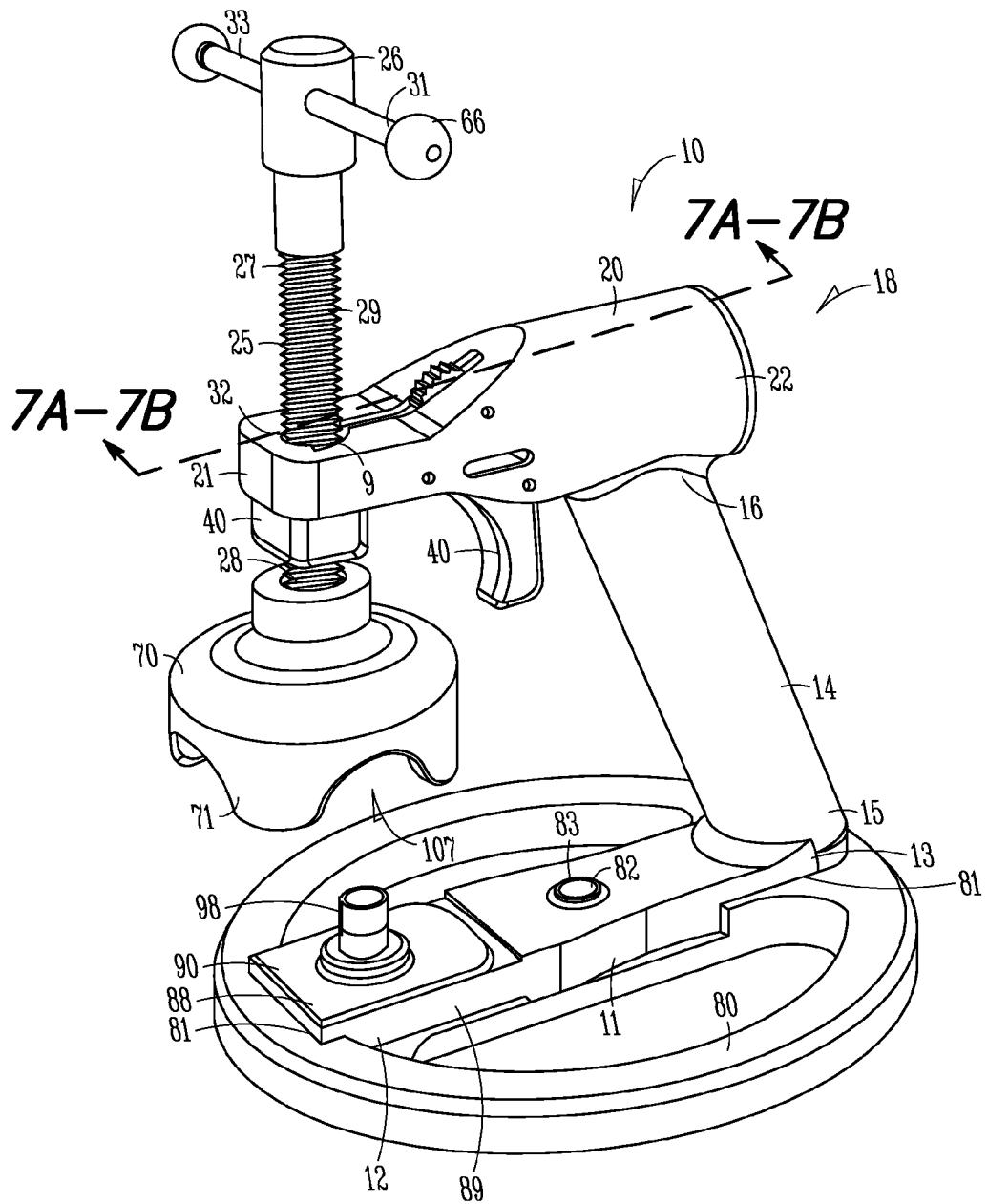
FIG. 6 illustrates an isometric view of an insert press, as constructed in accordance with at least one embodiment.

FIG. 6 illustrates an isometric view of insert press 10. The insert press 10 can be placed in a table base 80 to provide operation on a substantially flat surface. The insert press 10 can include two main structures: the threaded shaft 25 and the press housing 18. The press housing 18 can include a body member 20, a handle member 14, a lower member 11, and a trigger member 40. (note because the insert press 10 can be held in any orientation, the use of words such as "horizontal", "vertical", "upper", "lower", "forward", "rear" etc. are for the purposes of description only and should not be construed as limiting). The lower member 11 can include a forward end 12 and rear end 13. The rear end 13 can be connected to a lower end 15 of the handle member 14. The table base 80 can include one or more cut outs 81 sized and shaped to receive and secure the lower member 11. The table base 80 can include a handle post 82 which can be a protruding member of any shape that can fit inside a lower member aperture 83 and can operate to help secure the insert press 10 to the table base 80.

The forward end 12 has been described above and illustrated in FIG. 4. In FIG. 6 an attachment 88 such as a cone adapter 90 can be installed in the forked member 89. The cone adapter 90 can include an insert press post 98 sized and shaped to engage an aperture (not pictured) on a lower surface of a prosthetic component such as a femoral head 93 (See FIG. 3). The attachment 88 can be configured to operate with any type of prosthetic component. The handle member 14 can be sized and shaped to be comfortably held by one hand and can extend upwardly to an upper end 16. The upper end 16 can be attached to the body member 20. As illustrated in FIG. 6, the upper end 16 can be attached at a body rear end 22 of the body member 20. Attachment points for the handle member 14 to the body member 20 can vary, such as being attached to the very back or a side of the body member 20.

The body member 20 can include a body forward end 21 opposite the body rear end 22. The body forward end 21 can include a body aperture 32 which can form a portion of a bore 9 which can allow a threaded shaft 25 to be positioned directly above the forward end 12 of the lower member 11. Located at a position on or in the body member 20, a trigger member 40 can provide a mechanism that can allow the threaded shaft 25 to be moved upwardly and downwardly in body member 20 without engaging any threaded members. The trigger member 40 can also be positioned in a latched position 53 (See FIG. 7B), whereby threads included in a forward end of the trigger member 40 engage shaft threads 29 on the threaded shaft 25. The latched position 53 of the trigger member 40 can also cause the threaded shaft 25 to be pressed forward against threads in the body forward end 21 of the press body 20 (See FIG. 7B). The threaded shaft 25 can extend longitudinally from an upper portion 26 to a middle portion 27 and to a lower portion 28 (See FIG. 7B). Portions of the threaded shaft 25 such as the middle portion 27 can include shaft threads 29. The upper portion 26 can include a threaded shaft handle 31 which can aid in the rotation of the threaded shaft 25. The threaded shaft handle 31 is illustrated as a longitudinal rod 33 extending through the threaded shaft 25 and can include spherical knobs 66 disposed at the ends of the threaded shaft handle 31. In another example the threaded shaft handle can be a knob, a drivable member such as a hex or nut or other such means to rotate the threaded shaft 25. The threaded shaft can be rotated by an electric or pneumatic motor.

An insert driver 70 can be removably attached to the lower portion 28. The insert driver 70 can be sized and shaped to securely engage an insert 75 (See FIG. 3). Inserts 75 can be available in a range of dimensions and a kit of insert drivers 70 can be available to accommodate such dimension variations. The insert driver 70 can include lobes 71 and driver cut-outs 107 which can allow visual and tactile access to the insert 75 as the insert driver 70 presses an insert 75 onto a femoral head 93 (See FIG. 3).

Figure 7A:
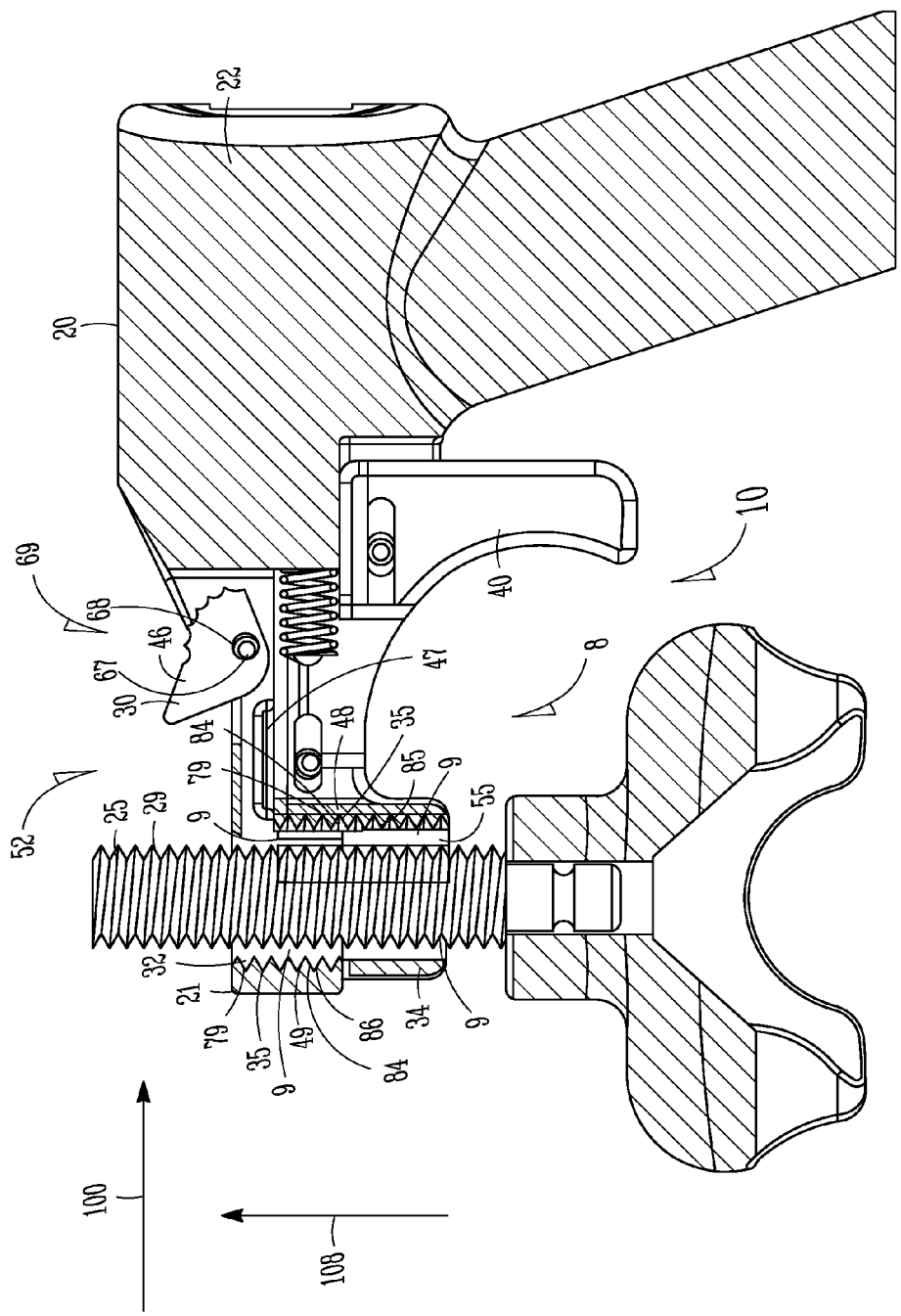
FIG. 7A illustrates a cross-sectional view 7A-7A of FIG. 6, as constructed in accordance with at least one embodiment.
Figure 7B:
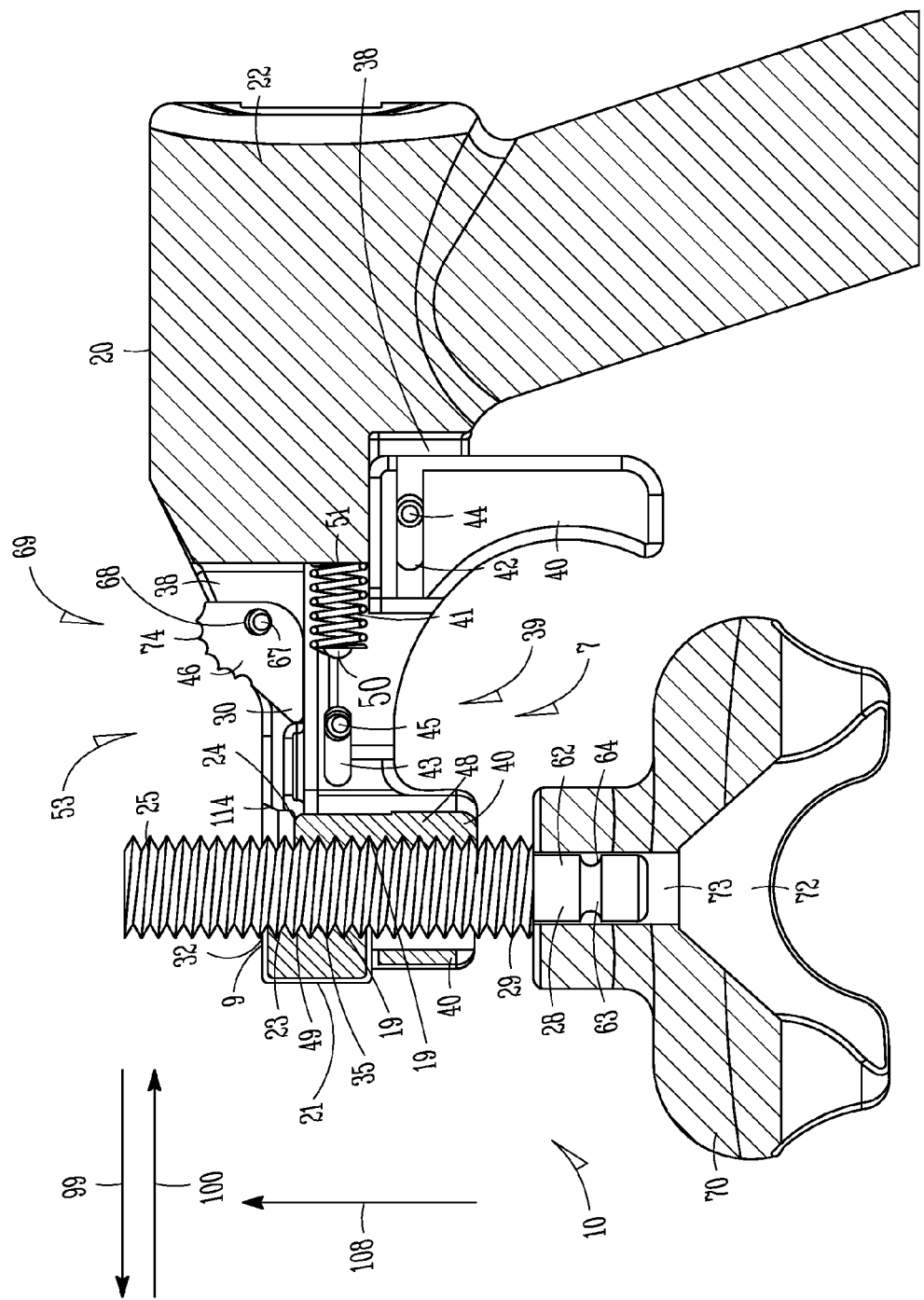
FIG. 7B illustrates a cross-sectional view 7B-7B of FIG. 6, as constructed in accordance with at least one embodiment.

FIG. 7A illustrates a cross-sectional view 7A-7A of FIG. 6, as constructed in accordance with at least one embodiment. FIG. 7B illustrates a cross-sectional view 7B-7B of FIG. 6, as constructed in accordance with at least one embodiment. FIGS. 7A and 7B illustrate how one particular type of bore such as bore 9 can be transformed from a second condition such as second condition 8 (See FIG. 7A) to a first condition such as first condition 7 (See FIG. 7B) or from a first condition to a second condition.

The bore 9 can include a body aperture 32 and a trigger aperture 55. The bore 9 can be formed partially in the body member 20 and partially in the trigger member 40. The bore 9 can include bore surfaces 79 that are disposed on more than one component of the prosthetic insert press 10, for example, such as on the body member 20 and/or on the trigger member 40. The bore 9 can include wall sections 84 that can include non-circumferential threads 35, such as a first wall section 85 disposed on the trigger member 40 and a second wall section 86 disposed on the body member 20. In a second condition 8, a trigger member 40 has been retracted in a rearwards direction 100 towards the body rear end 22. In the second condition 8, non-circumferential threads 35 in the body forward end 21 and non-circumferential threads 35 on the trigger member 40 can be disengaged from shaft threads 29. In the second condition 8, the threaded shaft 25 can be moved in a proximal/distal direction 108 without having to rotate the threaded shaft 25. In the second condition 8 the threaded shaft 25 can be moved up or down quickly to position an insert driver 70 on top of an insert 75, or to provide clearance so that a prosthetic component/insert assembly 77 (See FIG. 3) can be removed from the insert press 10. The trigger member 40 is shown in more detail in FIG. 8.

Figure 8:
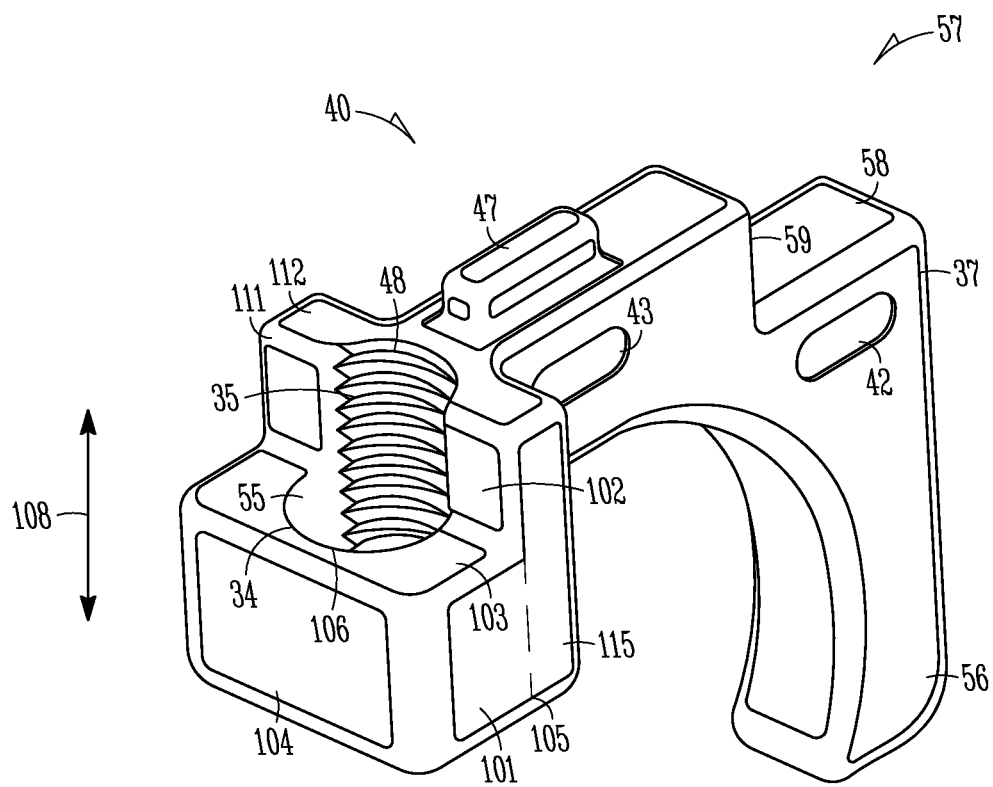
FIG. 8 illustrates an isometric view of a trigger member, as constructed in accordance with at least one embodiment.

In FIG. 7B, a trigger assembly 39 can include the trigger member 40, a biasing element 41, a latch 46, a rear pin 44 and a forward pin 45. The trigger assembly 39 can be positioned in a cavity 38 (note: parts of cavity 38 are filled with the trigger assembly 39) included in the body member 20. The cavity 38 can be formed to partially encase the trigger member 40 and biasing element 41 and allow the trigger member 40 to move in a forward direction 99 and rearward direction 100. In an example, the trigger member 40 can include a forward trigger slot 43 and a rear trigger slot 42. The slots 42 and 43 can be slidably engaged with a forward pin 45 and a rear pin 44. The pins 45 and 44 can be securely fixed to the body member 20. Such a configuration of slots on the trigger member 40 and pins in the body member 20 could be reversed. Other configurations of slidable engagement between the trigger member 40 and the body member 20 are contemplated such as a cylindrical trigger member within a tubular cavity of a body member 20. Referring to FIG. 8, towards the rear trigger end 37, the trigger member 40 can include a horizontal surface 58 and a vertical surface 59 which can connect and define a trigger cutout 57. The trigger cutout 57 can be sized and shaped to receive the biasing element 41 (See FIG. 7B) which can be in the form of a spring or some other such elastomeric means. The biasing can be accomplished by air pressure, hydraulic pressure or by a small electric motor. In FIG. 7B, the biasing element 41 can include a first end 50 and extend to a second end 51 opposite the first end 50. The first end 50 can engage the vertical surface 59 (See FIG. 8) of the trigger member 40 and the second end 51 can engage a surface of the body member 20. As the trigger member 40 is retracted in a direction towards the body rear end 22 of the body 20 a biasing force created by compression of the biasing element 41 can increase.

Referring to FIG. 8, the trigger member 40 can include structure defining a vertically disposed trigger aperture 55. In an example, the trigger aperture 55 can include a moveable threaded portion 48 which can be a series of partial, unconnected threads, or non-circumferential threads 35 on the rear portion of the trigger aperture 55. The forward portion of the trigger aperture 55 can be an unthreaded portion 34 and can be smooth and/or unthreaded. The trigger member 40 can be configured with a notched block member 101 which can have an L-shape 115 including a vertical forward face 102 and a horizontal proximal face 103. A top face 112 of the notched block member 101 can intersect the vertical forward face 102 at a corner 111. The trigger aperture 55 can be oriented in a proximal/distal direction 108 and can form a portion of the bore 9 through which the threaded shaft 25 extends (See FIG. 7A). An unthreaded portion 34 can have a larger diameter than the moveable threaded portion 48 so that when the trigger member has been retracted into a second condition 8 (See FIG. 7A), this portion of the trigger member 40 will not engage or interfere with shaft threads 29 on the threaded shaft 25. The unthreaded portion 34 can aid in moving the threaded shaft 25 rearward and away from mating threads in the body member 20 when the trigger member 40 is retracted and the bore 9 (See FIG. 7A) is transformed into a second condition 8. A forward section 104 of the notched block member 101 extends forward from illustration line 105. This forward section 104, which can include a forward portion 106 of the cylindrically shaped trigger aperture 55, need not be present in the trigger member 40.

A latch boss 47 can be disposed on a surface of the trigger 40. In an example, the latch boss 47 can be disposed on a surface located between the trigger aperture 55 and the trigger cutout 57. Referring to FIGS. 7A-B, the latch 46 can include a hinge mechanism 69 allowing the latch 46 to be moved from a latched position 53 to an unlatched position 52. In an example, the hinge mechanism 69 includes a latch pin 67 secured to the body 20 and moveably engaging a latch 46 on aperture 68. In an example, a surgeon or technician can manipulate the latch 46 by moving serrations 74 rearward so that a forward portion 30 of the latch 46 disengages from the latch boss 47, or by moving serrations 74 in a forward direction, so that the forward portion 30 of the latch 46 engages the latch boss 47 and prevents further movement of the trigger 40.

As illustrated in FIG. 7B, the latch boss 47 can provide a surface that the latch 46 can engage when in the latched position 53 and can lock the trigger member 40 in a forward biased position whereby the moveable threaded portion 48 of the trigger member 40 engages the shaft threads 29. As the trigger member 40 presses forward against the threaded shaft 25, the forward side of the threaded shaft 25 is engaged with a fixed threaded portion 49 of the body forward end 21. In an example, the fixed threaded portion 49 can be a series of unconnected thread portions or non-circumferential threads 35 formed in a forward half 23 of the body aperture 32. A rearward half 24 of the body aperture 32 can be unthreaded and can provide a space that can be occupied by portions of the threaded shaft 25 when the trigger member 40 is refracted. The aperture 32 can include a bevel 114 formed in the rearward half 24.

When the trigger member 40 is in a latched position 53, the combination of the forward position of the moveable threaded portion 48 and the fixed threaded portion 49 creates an aperture substantially surrounding the threaded shaft 25 with mating threads 19. The threaded shaft 25 can operate by rotation to provide pressure against an insert 75 to press it onto a prosthetic component such as a femoral head 93 (See FIG. 3) As illustrated in FIG. 7B, some portions of the fixed threaded portion 49 of the body forward end 21 can directly oppose portions of the moveable threaded portion 48 of the trigger member 40. In FIG. 7A, if the latch 46 is raised to an unlatched position 52, the trigger member 40 is no longer locked in place and can be moved. If the trigger member 40 is retracted towards the body rear end 22 of the body 20, the moveable threads 48 can disengage from the threaded shaft 25 and the unthreaded portion 34 can simultaneously operate to pull the threaded shaft 25 away from the fixed threaded portion 49 so that the fixed threaded portion also disengages from the threads 29 of the threaded shaft 25. With the trigger member 40 retracted, the threaded shaft 25 can now be moved in a proximal/distal direction 108 without rotation.

FIG. 7B also illustrates a connection between the threaded shaft 25 and the insert driver 70. The insert driver can include a bore 73 sized to receive the lower portion 28 of the threaded shaft 25. The lower portion 28 can include a smooth portion 62 and a groove 63. A spring loaded detent ball 64 located in the bore 73 can provide a quick release locking mechanism to hold the insert driver 70 to the threaded shaft 25 by engaging the groove 63. Other fastening means, such as threading, can be used to connect the insert driver 70 to the threaded shaft 25. The insert driver can include a concavity 72 sized and shaped to receive an insert 75 (See FIG. 2).

Figure 9:
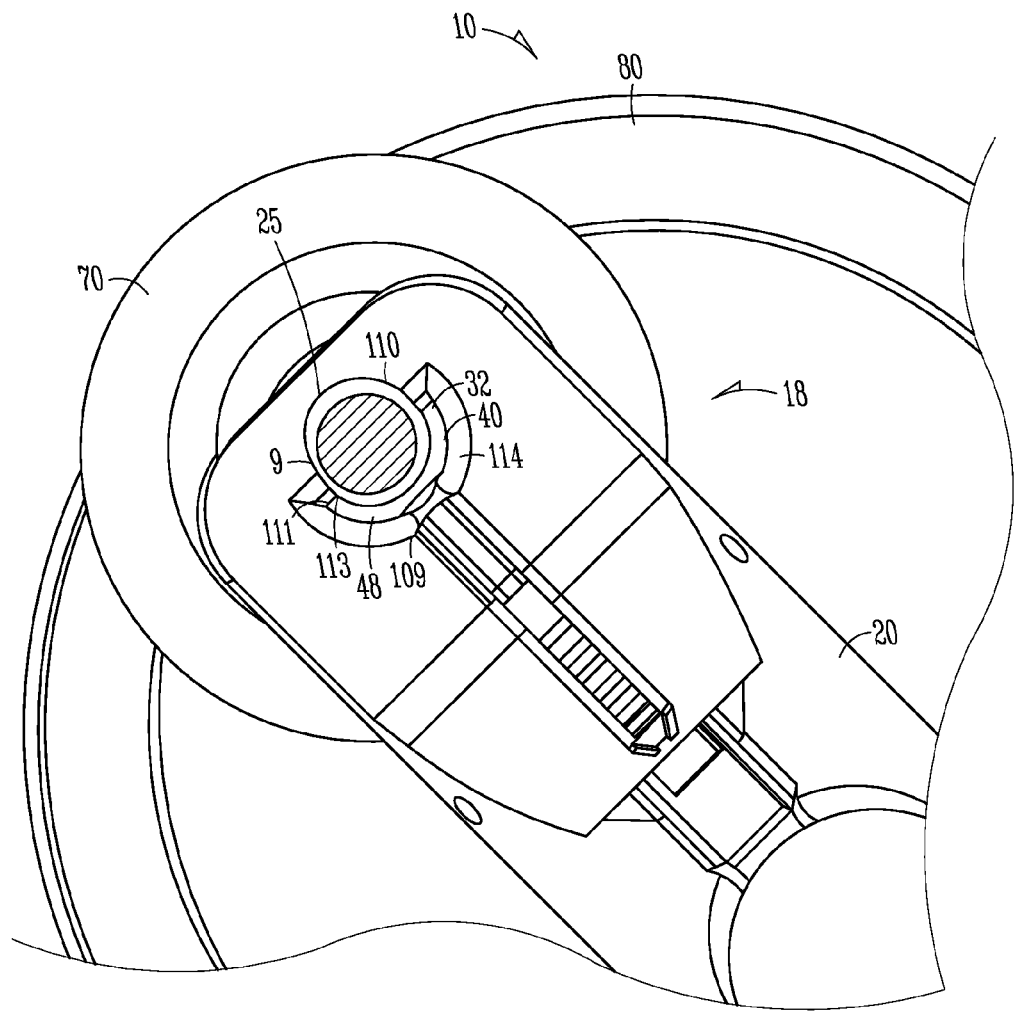
FIG. 9 illustrates a cross-sectional view 9-9 of FIG. 3, as constructed in accordance with at least one embodiment.

FIG. 9 illustrates a cross-sectional view 9-9 of FIG. 3, as constructed in accordance with at least one embodiment. FIG. 9 illustrates a view from the top of an insert press 10 where the top portions of the threaded shaft 25 have been cut away to give a better view of the body aperture 32 and the bore 9. The shape of the body aperture 32 at the top of the body 20 can include a forward half portion 110 and a rear half portion 109. In FIG. 9, the bore 9 is illustrated in a first condition 7 and a moveable threaded portion 48 of the trigger member 40 can be seen engaged with the threaded shaft 25 through the rear half portion 109 of the body aperture 32. The forward half portion 110 can have a diameter that approximates the diameter of the threaded shaft 25 so that threads in the body forward end 21 (See FIG. 7A-B) can engage the threaded shaft 25. The diameter of the rear half portion 109 can be larger than the diameter of the threaded shaft 25, so that when the bore 9 is transformed to a second condition 8 (See FIG. 7A), the threaded shaft 25 has clearance from any threads in the press housing 18, the bore 9, the trigger member 40 or the body 20. The trigger member 40 can include a hemispherical shape 113 that approximates the diameter of the threaded shaft 25 and the corner 111 relates to corner 111 of FIG. 8. The aperture 32 can include a bevel 114 formed in the rear half portion 109.

Figure 10:
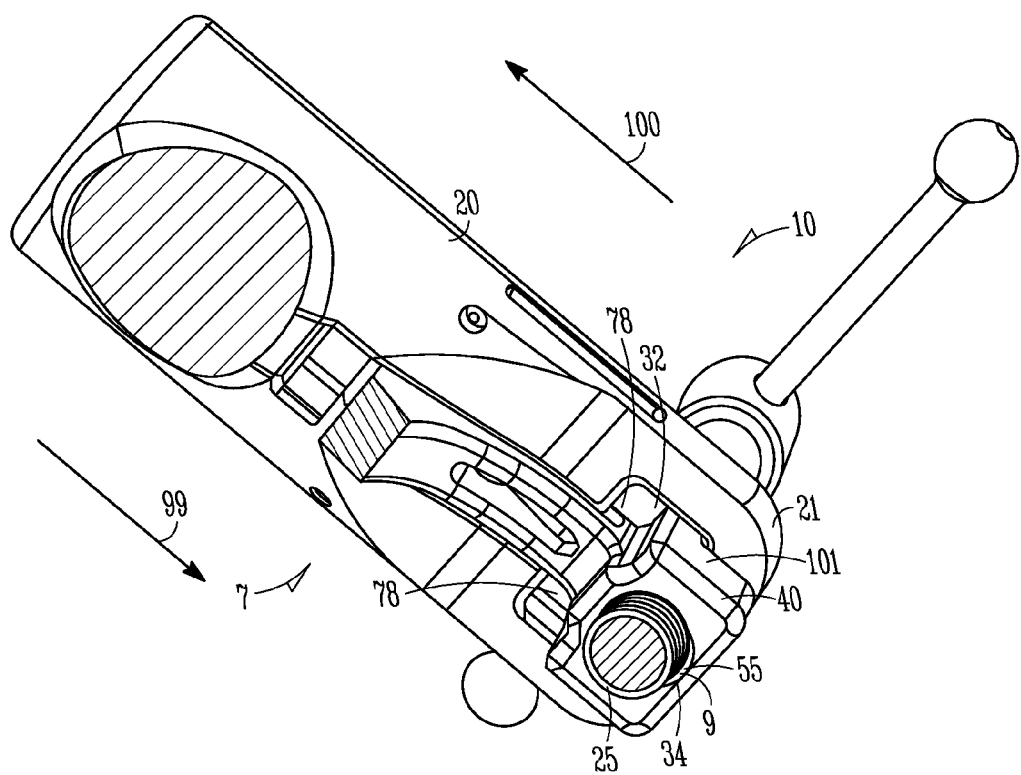
FIG. 10 illustrates a cross-sectional view 10-10 of FIG. 3, as constructed in accordance with at least one embodiment.

FIG. 10 illustrates a cross-sectional view 10-10 of FIG. 3, as constructed in accordance with at least one embodiment. FIG. 10 is an isometric view of an insert press 10 viewed from the bottom with portions of the threaded shaft 25 and the insert driver 70 (See FIG. 3) cut away. In this example, the bore 9 can include openings in both the trigger member 40 and the body 20. FIG. 10 illustrates how the notched block member 101 of the trigger member 40 can engage the body member 20 at the body forward end 21. As the trigger member 40 is moved in a forward direction 99, the trigger member 40 can push the threaded shaft 25 until it engages a fixed threaded member 49 in the body forward end 21 (See FIG. 7B). A space 78 forming portions of the aperture 32 in the body member 20 can allow movement of the trigger member 40 in a rearward direction 100 when the bore 9 is transformed from a first condition 7 as illustrated in FIG. 10 to a second condition 8 (See FIG. 7A). The unthreaded portion 34 of the trigger aperture 55 can have clearance so as not to engage the threaded shaft 25 when the bore 9 is in the first condition 7. When the trigger member 40 is moved in a rearward direction 100 the unthreaded portion 34 can engage the threaded shaft 25 and aid in disengaging the threaded shaft 25 from non-circumferential threads 35 in a fixed threaded portion 49 of the forward body end 21 (See FIG. 7B).

It is fully contemplated by the present disclosure that other devices and methods of transforming the bore 9 from a first condition 7 to a second condition 8 can be configured. In an example, an insert press 10 can have more than one moveable partially threaded member. In an example, an insert press 10 can have one or more moveable partially threaded members that instead of moving as described above, are moveable with the aid of a rotating member, such as in tightening or loosening a drill chuck. In an example, the bore 9 can be transformed by multiple movable members advancing and retracting from the threaded shaft 25 from various angular directions, not limited to the forward and rearward directions described above. In an example, structures towards the rear side of the threaded shaft such as the trigger member 40 described above, can be stationary and structures having partially threaded portions in the body member can include moveable threaded portions.

Any one or combination of the devices disclosed above and in FIGS. 1-10 can be used in a method of installing a prosthetic insert on a prosthetic component. An insert can be placed over a prosthetic component, such as a femoral head. A bore can be transformed from a first condition whereby threads on a threaded shaft are engaged with threads in a press housing to a second condition whereby threads on the threaded shaft and on the press housing are not engaged. A trigger member can be retracted and a threaded shaft member can fall freely or be moved in a bore without rotating a threaded shaft member so that an insert driver can engage an insert. A trigger member can be released and a moveable threaded member on the trigger member can engage threads on the threaded shaft. The trigger member can also push the threaded shaft member towards stationary non-circumferential threads on a portion of a bore in a body of the press housing. The bore though which the threaded shaft extends can be transformed so that the threaded shaft can be threadably translated or moved up and down by rotating the threaded shaft. As the threaded shaft is translated distally or downward, an insert driver can be pressed onto a prosthetic component such as a femoral head. After pressing, the trigger member can be retracted, which can transform the bore and can disengage any threads disposed on a moveable member or a stationary member from the threads disposed on the threaded shaft. With the threads of the threaded shaft disengaged, the threaded shaft can be translated in the bore without the need of rotation and a prosthetic component/insert assembly can be quickly removed from the insert press.

The above Detailed Description includes references to the accompanying drawings, which form a part of the Detailed Description. The drawings show, by way of illustration, specific embodiments in which the present insert press and method can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the term "patient" is intended to include mammals, such as for human applications or veterinary applications.

In the appended claims, the terms "including" and "in which" are used as the plain-English equivalents of the respective terms "comprising" and "wherein." Also, in the following claims, the terms "including" and "comprising" are open-ended, that is, an assembly, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An insert press, comprising:
a threaded shaft having a distal end;
an insert driver disposed at the distal end of the threaded shaft; and
a press housing providing a bore through which the threaded shaft extends, the bore transformable from a first condition in which the threaded shaft is threadably translatable in the bore to a second condition in which the threaded shaft is non-threadably translatable in the bore,
wherein the bore is transformable from the first condition to the second condition by straight linear movement of a first wall section of the bore in a first direction along a first plane, the first wall section having a surface with non-circumferential threads, the bore including a second wall section opposite the first wall section which moves concurrently with the first wall section in the first direction along the first plane when transforming the bore from the first condition to the second condition.

2. The insert press of claim 1, wherein the press housing includes a body member having a threaded shaft end and a handle end, the press housing further including a trigger member engaging the body member and movable relative to the body member.

3. The insert press of claim 1, wherein the bore is transformable from the first condition to the second condition by straight linear movement of at least two wall sections of the bore that each have a surface with non-circumferential threads.

4. An insert press, comprising:
a threaded shaft having a distal end;
an insert driver disposed at the distal end of the threaded shaft; and
a press housing providing a bore through which the threaded shaft extends, the bore transformable from a first condition in which the threaded shaft is threadably translatable in the bore to a second condition in which the threaded shaft is non-threadably translatable in the bore, wherein the press housing comprises:
a lower member having a forward end and a rear end;
a handle member having a distal end and a proximal end, wherein the distal end extends from the rear end of the lower member;
a body member having a threaded shaft end and a handle end, wherein the handle end extends from the proximal end of the handle member; and
a trigger member engaging the body member and movable relative to the body member.

5. The insert press of claim 1, wherein the press housing further comprises a body member and a trigger member, wherein the bore is partially provided by the body member and partially provided by the trigger member.

6. The insert press of claim 4, wherein the body member provides a bore surface having non-circumferential threads.

7. The insert press of claim 4, wherein the trigger member provides a bore surface having non-circumferential threads.

8. An insert press, comprising:
a threaded shaft having a distal end;
an insert driver disposed at the distal end of the threaded shaft; and
a press housing providing a bore through which the threaded shaft extends, the bore transformable from a first condition in which the threaded shaft is threadably translatable in the bore to a second condition in which the threaded shaft is non-threadably translatable in the bore, the press housing including a body member having a threaded shaft end and a handle end, the press housing further including a trigger member engaging the body member and movable relative to the body member, wherein the body member provides a bore surface having non-circumferential threads and the trigger member provides a bore surface having non-circumferential threads and wherein, when the bore is transformed into the first condition, the non-circumferential threads of the body member engage the threaded shaft and the non-circumferential threads of the trigger member engage the threaded shaft.

9. An insert press, comprising:
a threaded shaft having a distal end;
an insert driver disposed at the distal end of the threaded shaft; and
a press housing providing a bore through which the threaded shaft extends, the bore transformable from a first condition in which the threaded shaft is threadably translatable in the bore to a second condition in which the threaded shaft is non-threadably translatable in the bore, the press housing including a body member having a threaded shaft end and a handle end, the press housing further including a trigger member engaging the body member and movable relative to the body member, wherein the trigger member further comprises an aperture through which the threaded shaft extends, wherein the aperture and the bore are coaxial, the aperture sized to allow the threaded shaft to non-threadably translate in the bore when the bore is in the second condition.

10. The insert press of claim 7, wherein the trigger member further comprises a shaft end and a lever end, wherein the shaft end provides a shelf member having a horizontal surface and a vertical surface, the vertical surface comprising the non-circumferential threads of the bore surface provided by the trigger member which engage the threaded shaft in the first condition.

11. The insert press of claim 4, further comprising a latching means engaging the press housing body and configured to engage the trigger member and secure the trigger member in the first condition.

12. The insert press of claim 11, wherein the latching means engages the trigger member at a latch boss which extends from a surface of the trigger member.

13. The insert press of claim 4, further comprising a biasing means that engages the trigger member and the body member and biases the trigger member in the first condition.

14. The insert press of claim 1, further comprising a table base configured to engage with and stabilize the press housing.

15. The insert press of claim 8, wherein the trigger member further comprises an aperture through which the threaded shaft extends, wherein the aperture and the bore are coaxial, the aperture sized to allow the threaded shaft to non-threadably translate in the bore when the bore is in the second condition.

16. The insert press of claim 8, wherein the bore is transformable from the first condition to the second condition by straight linear movement of at least one wall section of the bore having a surface with non-circumferential threads.

17. The insert press of claim 9, wherein the bore is transformable from the first condition to the second condition by straight linear movement of at least one wall section of the bore having a surface with non-circumferential threads.

* * * * *